US009757109B2

(12) United States Patent
Duggal et al.

(10) Patent No.: US 9,757,109 B2
(45) Date of Patent: Sep. 12, 2017

(54) ORGANIC LIGHT EMITTING DIODE ILLUMINATED SURGICAL RETRACTOR (75) Inventors: Anil Duggal, Bright's Grove (CA); James E. Lyles, Jamaica, NY (US)

(73) Assignee: Illumix Surgical Canada Inc., Bright's Grove, ON (CA)

( * ) Notice: Subject to any disclaimer, the term of this patent is extended or adjusted under 35 U.S.C. 154(b) by 64 days.

(21) Appl. No.: 13/311,031

(22) Filed: Dec. 5, 2011

(65) Prior Publication Data

US 2012/0149992 A1 Jun. 14, 2012

Related U.S. Application Data (60) Provisional application No. 61/421,882, filed on Dec. 10, 2010, provisional application No. 61/475,904, filed on Apr. 15, 2011.

(51) Int. Cl.
*A61B 1/32* (2006.01)
*A61B 17/02* (2006.01)
*A61B 17/00* (2006.01)
*A61B 90/30* (2016.01)

(52) U.S. Cl.
CPC .......... *A61B 17/0206* (2013.01); *A61B 17/02* (2013.01); *A61B 2017/00946* (2013.01); *A61B 2090/309* (2016.02)

(58) Field of Classification Search
CPC ....................... A61B 17/0206; A61B 2019/521
USPC ........ 600/201, 203, 210–213, 223, 245, 199
See application file for complete search history.

(56) References Cited

U.S. PATENT DOCUMENTS

| 5,613,751 | A | * | 3/1997 | Parker et al. ................. 362/627 |
| 6,428,473 | B1 | | 8/2002 | Leonard et al. |
| 6,730,019 | B2 | | 5/2004 | Irion |
| 7,106,396 | B2 | * | 9/2006 | Suzuki ........................... 349/74 |
| 7,195,482 | B2 | * | 3/2007 | Scott ............................. 433/29 |
| 7,306,559 | B2 | | 12/2007 | Williams |
| 7,307,785 | B2 | | 12/2007 | Obrebski et al. |
| 7,626,327 | B2 | | 12/2009 | Shimada et al. |
| 2003/0095781 | A1 | | 5/2003 | Williams |
| 2005/0171408 | A1 | | 8/2005 | Parker |
| 2006/0069314 | A1 | * | 3/2006 | Farr ............................. 600/179 |
| 2006/0217596 | A1 | * | 9/2006 | Williams ..................... 600/245 |
| 2006/0217597 | A1 | | 9/2006 | Vayser et al. |
| 2006/0229593 | A1 | | 10/2006 | Vayser et al. |
| 2007/0060795 | A1 | | 3/2007 | Vayser et al. |
| 2007/0276191 | A1 | | 11/2007 | Selover et al. |
| 2007/0293729 | A1 | | 12/2007 | Grey et al. |

(Continued)

FOREIGN PATENT DOCUMENTS

EP 2315507 A1 4/2011
EP 2317831 A1 5/2011

(Continued)

*Primary Examiner* — Jan Christopher Merene
*Assistant Examiner* — Atiya Mahmud
(74) *Attorney, Agent, or Firm* — Soody Tronson; STLGip Law Firm (57) ABSTRACT A retractor having a housing having a handle portion at a first end and a blade portion at a second, opposite end. The retractor includes a light system having an organic light source for illuminating the blade portion. The light system is positioned within the housing such that it is fully encased by said housing. A pair of polarized light panels are attached to the blade portion for varying direction of light from the blade portion.

18 Claims, 10 Drawing Sheets (56) References Cited

U.S. PATENT DOCUMENTS

| | | |
|---|---|---|
| 2008/0081952 A1 | 4/2008 | Josephberg |
| 2008/0108877 A1 | 5/2008 | Bayat |
| 2008/0303982 A1* | 12/2008 | Jin et al. .......................... 349/69 |
| 2009/0036744 A1* | 2/2009 | Vayser .......................... 600/182 |
| 2009/0203969 A1 | 8/2009 | Cohen et al. |
| 2010/0016844 A1 | 1/2010 | Patel, Jr. |
| 2010/0191067 A1 | 7/2010 | Chen |
| 2010/0249528 A1* | 9/2010 | Vayser et al. ................. 600/245 |
| 2010/0312069 A1 | 12/2010 | Sutherland et al. |
| 2010/0317928 A1* | 12/2010 | Subramaniam ............... 600/245 |
| 2011/0011519 A1 | 1/2011 | De Vries |
| 2011/0100524 A1 | 5/2011 | van den Brand et al. |
| 2011/0171764 A1 | 7/2011 | Toonen et al. |
| 2011/0297996 A1 | 12/2011 | van den Brand et al. |

FOREIGN PATENT DOCUMENTS

| | | |
|---|---|---|
| EP | 2355144 A1 | 8/2011 |
| WO | 2008127110 A1 | 10/2008 |
| WO | 2009102201 A1 | 8/2009 |
| WO | 2010002252 A1 | 1/2010 |
| WO | 2011037460 A1 | 3/2011 |
| WO | 2011049455 A1 | 4/2011 |
| WO | 2011051234 A1 | 5/2011 |
| WO | 2011053128 A1 | 5/2011 |

* cited by examiner

ORGANIC LIGHT EMITTING DIODE ILLUMINATED SURGICAL RETRACTOR

This application claims the benefit of U.S. Provisional Patent Application Ser. No. 61/421,882, filed on Dec. 10, 2010, and U.S. Provisional Patent Application Ser. No. 61/475,904, filed on Apr. 15, 2011. the disclosure of each is incorporated herein by reference.

FIELD OF THE INVENTION

The present invention relates generally to retractors and, more particularly, to a retractor having an embedded organic light source, such as a flexible organic light emitting diode, for providing direct illumination for medical, dental, surgical or veterinarian procedures as well as for other uses in industrial applications.

BACKGROUND OF THE INVENTION

It is well known that illumination is required for nearly every medical, dental, surgical or veterinarian procedure as well as in other fields such as automotive repair, aviation, mining and other industrial applications. The most common approach for providing illumination is an overhead lighting system. Although an overhead lighting system provides some illumination for the procedure or other application, these type of systems suffer from multiple limitations. For example, overhead lighting systems must be constantly adjusted to provide for proper illumination of the desired area, which is time-consuming and inefficient. In addition, overhead lighting systems may provide insufficient illumination for surgeries in deeper cavities and anatomical recesses within the body or in situations where the light may be blocked by persons in the surgical area. Overhead lighting systems are also expensive and, thus, costly to repair and replace.

To address the limitations associated with overhead lighting systems, one approach is to incorporate a light source with a particular surgical instrument, such as a retractor. A retractor is an instrument that may be used by an operator for a variety of applications, such as actively separating the edges of a surgical incision or holding back underlying organs or tissues such that body parts under the incision may be accessed. The light source may be an incandescent lamp, halogen lamp or light emitting diode (LED).

An organic light emitting diode (OLED) is typically a monolithic, solid-state device having a series of organic thin films positioned between two thin-film conductive electrodes. When electricity is applied to the OLED, charge carriers (i.e., holes and electrons) are injected from the electrodes into the organic thin films. Under the influence of the electrical field, these carriers migrate through the device until they recombine to form excitons. Once formed, these excitons relax to a lower energy by giving off light and/or heat.

Generally, incorporating a light source with a surgical instrument involves attaching an external light source to the exterior of an existing retractor for providing illumination. For example, an illumination insert may be inserted through a surgical retractor or an illumination element may be mounted on or in a collar body or a surgical retractor pin. In addition, some surgical instruments conduct light into the surgical field by an external light source through a conductive material such as a fiber optic.

Although these devices may address some of the limitations of the overhead lighting system discussed above, they still suffer from significant limitations. Namely, these type of devices can be bulky due to the external light source being attached to the exterior of the surgical instrument, which makes it difficult for the operator to maneuver the device. These devices also have durability concerns as they may be easily damaged as the light source is not protected by a housing or other protective measure. Moreover, these devices do not allow for variable direction of light in the surgical field. Finally, it should be appreciated that a surgical environment requires a completely sterile environment. Since the light source is not self-contained in these devices, sterility is of greater concern with respect to the electronics associated with the light source being exposed.

Accordingly, a need is identified in the field of retractors for addressing and overcoming the foregoing limitations. Specifically, it is desirable to incorporate a light source in the form of an OLED directly into the retractor, such that it is a completely self-contained unit as well as being flexible and malleable. The OLED may be coupled with polarized light panels, which provide certain advantages over previously utilized light sources, such as providing optimal illumination for a variety of desired lighting conditions. The resulting retractor would aid in providing illumination in anatomical recesses and orifice surgery where previous light sources and external lighting systems were limited as well as lowering costs compared with current lighting systems.

SUMMARY OF THE INVENTION

The above-mentioned and other problems become solved by applying the principles and teachings associated with the hereinafter described organic light emitting diode (OLED) illuminated surgical retractor.

In accordance with one aspect of the disclosure, a retractor including a housing with a handle portion at a first end and a blade portion at a second, opposite end is provided. The retractor also includes a light delivery system having an organic light source for illuminating the blade portion. The light delivery system is positioned within the housing such that it is fully encased by the housing. A pair of polarized light panels are attached to the blade portion for varying direction of light from the blade portion. Preferably, the organic light source is an organic light emitting diode or a flexible organic light emitting diode.

Another related aspect of the disclosure is a surgical retractor including a power supply positioned within a handle, a retraction blade and a pair of polarized light panels. The surgical retractor also includes a light encasement housing connected to the distal end of the retraction blade and a retraction blade housing having a removable organic light emitting diode unit embedded within the housing for illuminating the retraction blade. The organic light emitting diode unit is positioned between the pair of polarized light panels such that light is radiated to a desired area of interest in a uniform intensity.

A further aspect of the disclosure is a flexible surgical retractor having a malleable retraction surface. The flexible surgical retractor also has a transparent, flexible housing encasing the malleable retraction surface. Further, a flexible organic light emitting diode unit is positioned within the malleable retraction surface for completely illuminating the surgical retractor.

Still other objects of the present invention will become apparent to those skilled in the art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects, all without departing from the invention. Accordingly, the drawings and description will be regarded as illustrative in nature and not as restrictive.

BRIEF DESCRIPTION OF THE DRAWINGS

The accompanying drawings incorporated in and forming a part of the specification, illustrates several aspects of the present invention, and together with the description serve to explain the principles of the invention. In the drawings.

DETAILED DESCRIPTION OF THE INVENTION

In the following detailed description, reference is made to the accompanying drawing that forms a part hereof, and in which is shown by way of illustration, specific embodiments in which the invention may be practiced. These embodiments are described in sufficient detail to enable those skilled in the art to practice the invention and like numerals represent like details in the various figures. Also, it is to be understood that other embodiments may be utilized and that process or other changes may be made without departing from the scope of the present invention. The following detailed description is, therefore, not to be taken in a limiting sense, and the scope of the present invention is defined only by the appended claims and their equivalents. In accordance with the present invention, an organic light emitting diode (OLED) illuminated surgical retractor is hereinafter described.

As discussed below, the light emitting diode used with various types of surgical retractors may be an organic light emitting diode (OLED), a flexible organic light emitting diode (FOLED), a transparent organic light emitting diode (TOLED), a stacked organic light emitting diode (SOLED) and/or a phosphorescent organic light emitting diode (PHOLED). The term OLED is used throughout this application should be construed in its broadest sense, which includes any of the various types of OLED's discussed above, including an ordinary OLED, a FOLED, a TOLED, a SOLED and/or a PHOLED.

Figure 1:
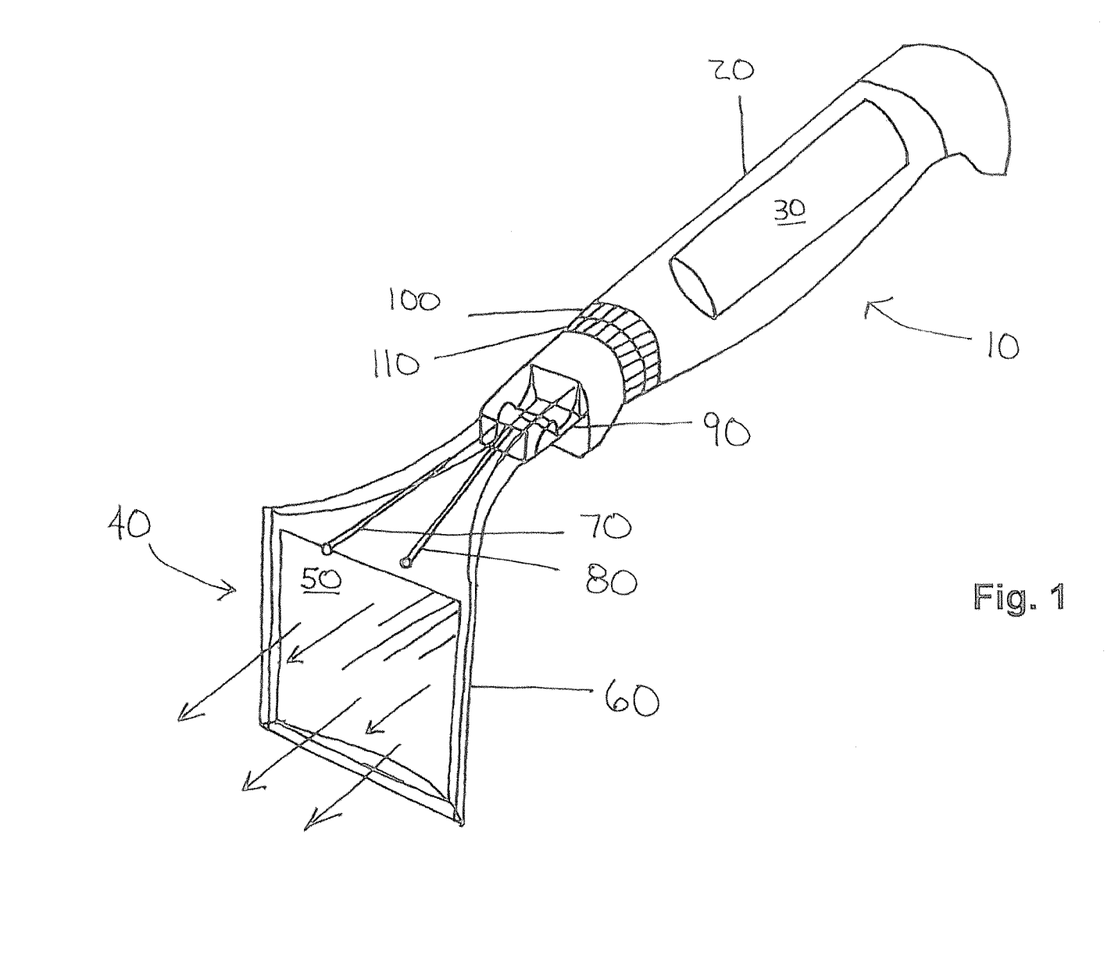
FIG. 1 is a perspective view in accordance with one embodiment of the present invention of an organic light emitting diode (OLED) illuminated retractor.
Figure 3:
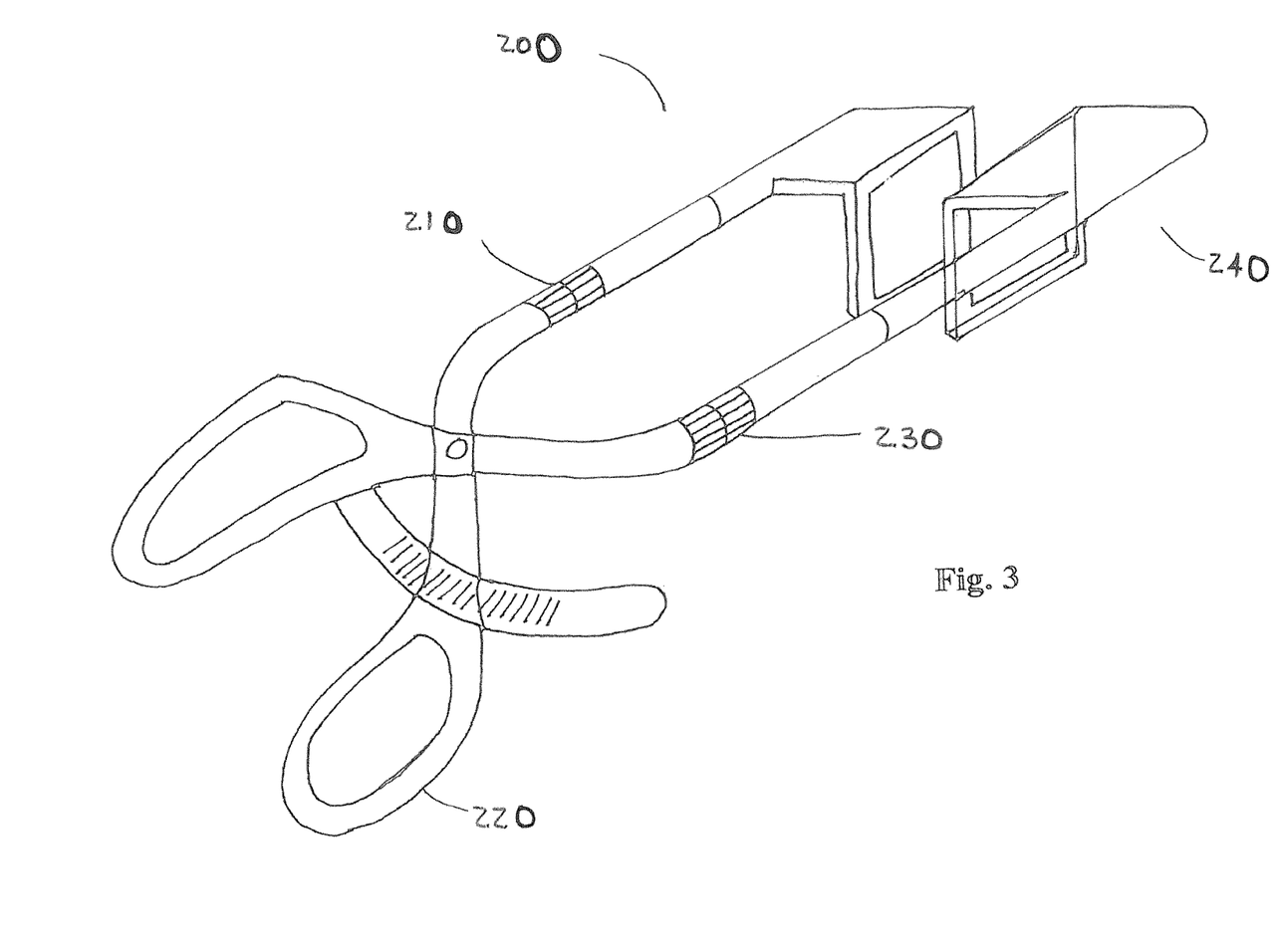
FIG. 3 is a perspective view in accordance with one embodiment of the present invention of an OLED illuminated retractor.

As shown in FIG. 1, a representative cavity-based surgical retractor 10, such as a Richardson-type intra-abdominal retractor incorporating OLED illumination of the retraction surfaces is illustrated. With reference to FIG. 3, it illustrates another type of retractor 200, namely, a skin/soft tissue retractor, such as a Weitlaner-type self-retaining tissue retractor incorporating OLED illumination of the retraction surfaces. Of course, it should be appreciated that the OLED technology discussed herein is capable of being applied to all other types of surgical retractors for different areas of surgery as well as in other fields, such as dentistry, veterinary medicine, automotive repair, aviation, mining and other industrial applications. For example, OLED technology may also be incorporated into system-based retractors (i.e., OMNI) and orifice-based retractors.

Figure 4:
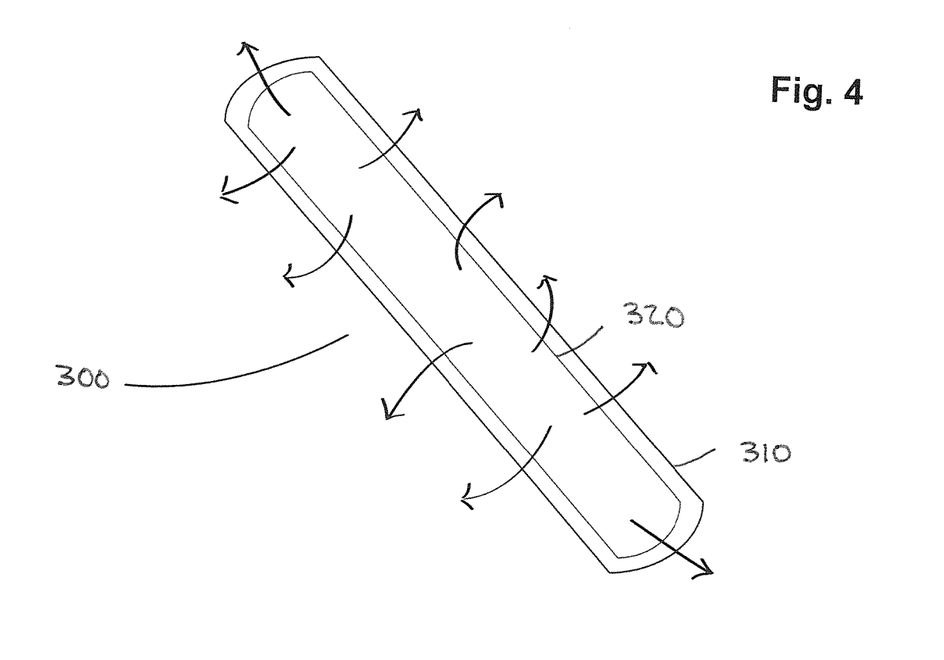
FIG. 4 is a perspective view in accordance with one embodiment of the present invention of a single OLED illuminated malleable retractor.
Figure 5:
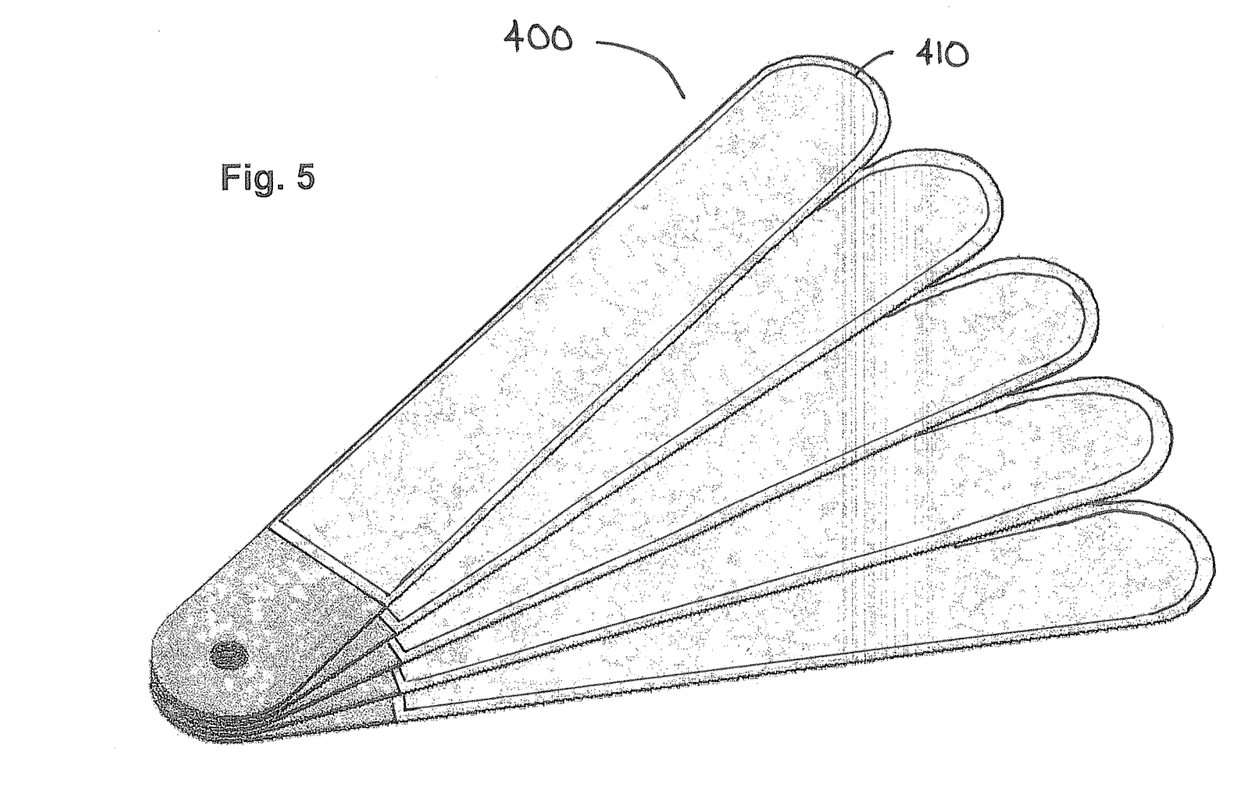
FIG. 5 is a perspective view in accordance with one embodiment of the present invention of a fan-shaped OLED illuminated malleable retractor.

As shown in FIG. 4, a single FOLED malleable retractor 300 is illustrated, which resembles a tongue depressor in shape and thickness. The malleable retractor 300 can be contorted to fit in a particular orifice, such as the floor of the orbit. Advantageously, the malleable retractor 300 has a body 310 wherein a central portion 320 may be illuminated with OLED's to improve the surgeon's view of the orifice (light is depicted by the arrows). With reference to FIG. 5, a fan-shaped FOLED malleable retractor 400 having an OLED illuminated portion 410 that is stackable is illustrated. As illustrated in FIGS. 4 and 5, the OLED-based retractors may be configured in numerous ways, such as having multiple blades that are stacked or having a single blade that is contorted to fit a specific shape.

Figure 6:
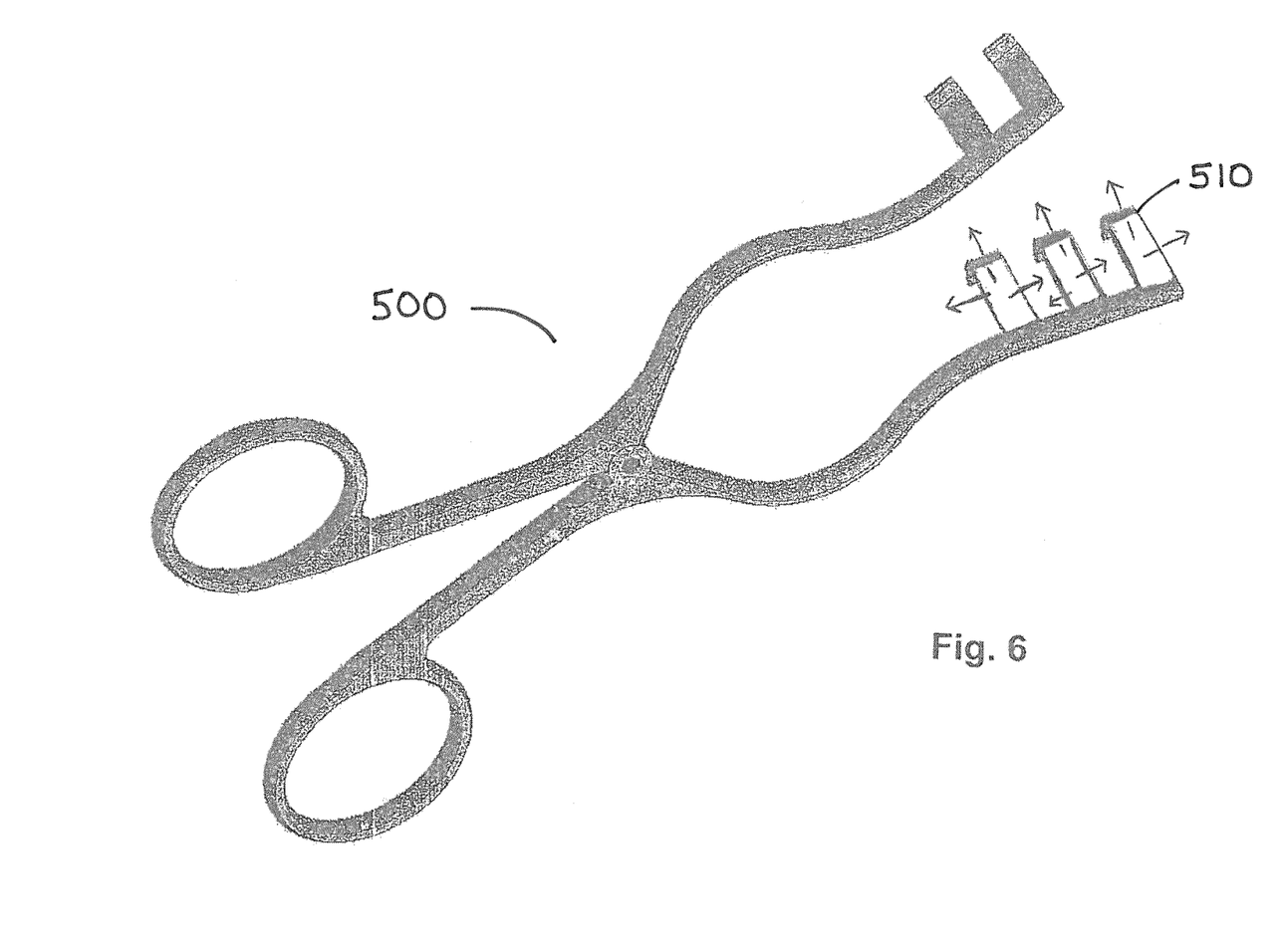
FIG. 6 is a perspective view in accordance with one embodiment of the present invention of an OLED illuminated retractor.
Figure 7A:
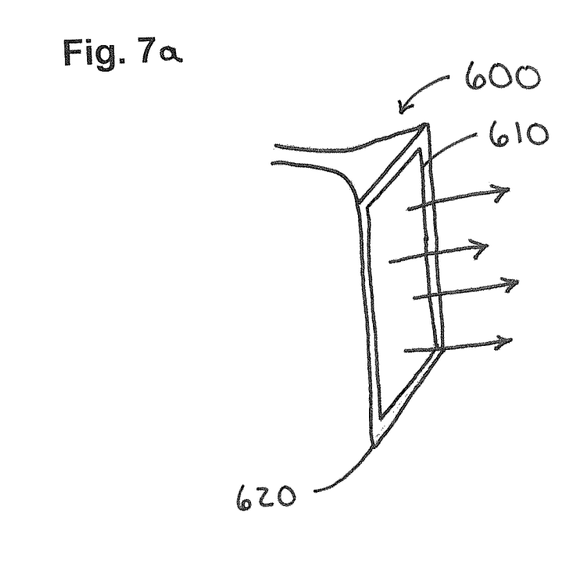
FIG. 7a is a partial cutaway view in accordance with one embodiment of the present invention of an OLED encased in a malleable retractor blade in a native configuration.
Figure 7B:
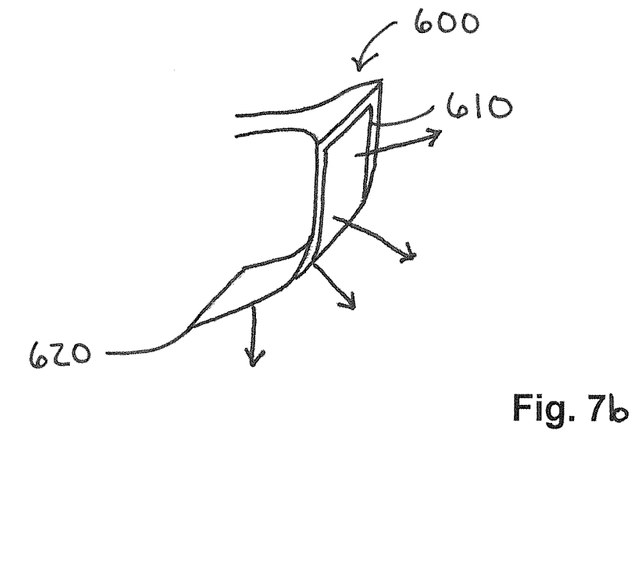
FIG. 7b is a partial cutaway view in accordance with one embodiment of the present invention of an OLED encased in a malleable retractor blade in a flexed configuration.
Figure 8:
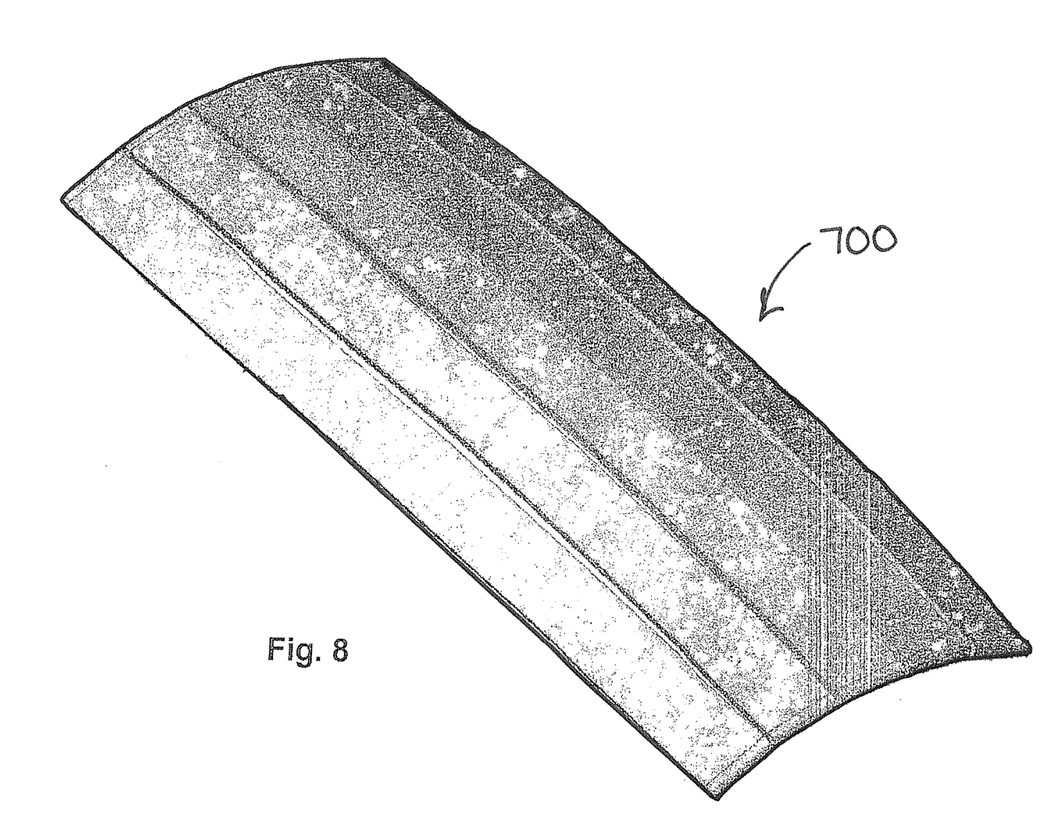
FIG. 8 is a perspective view in accordance with one embodiment of the present invention of an OLED illuminated retractor.
Figure 9:
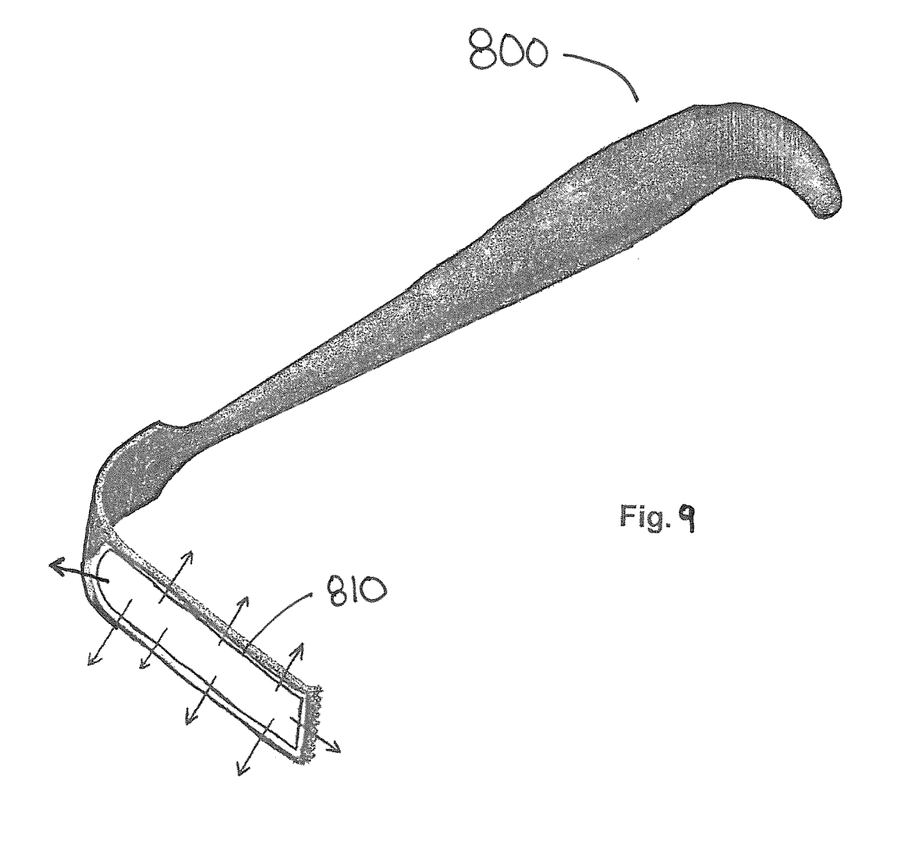
FIG. 9 is a perspective view in accordance with one embodiment of the present invention of an OLED illuminated retractor.
Figure 10:
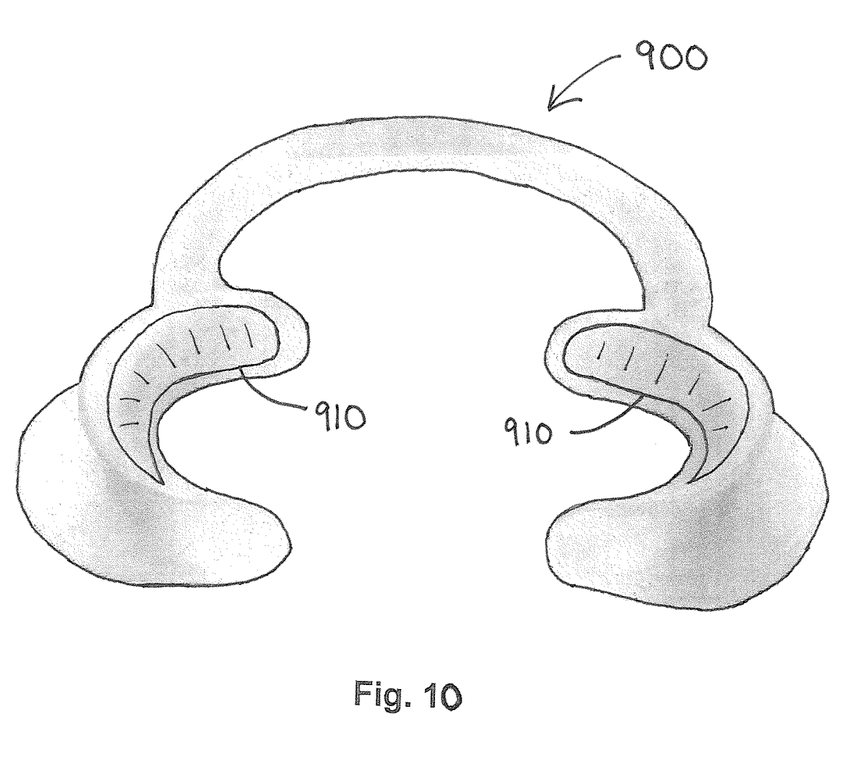
FIG. 10 is a perspective view in accordance with one embodiment of the present invention of a malleable OLED illuminated retractor.

Turning to FIGS. 6-10, various other types of retractors incorporating OLED, FOLED and/or TOLED technology are illustrated. For example, a Weitlaner retractor 500 with a plurality of teeth 510 is illustrated in FIG. 6. In FIGS. 7a and 7b, a FOLED encased in a malleable retractor blade 600 is illustrated in a native (FIG. 7a) and flexed confirmation (FIG. 7b) after pressure has been applied. The FOLED panels 610 are illustrated with arrows of illumination emanating and the retractor blade 620 closely resembles the handle retractor illustrated in FIG. 1. FIG. 8 illustrates an OLED light strip positioned on a retractor blade surface 700. Finally, another embodiment of a handle retractor 800 having an OLED illuminated blade surface 810 is illustrated in FIG. 9, while a dental/cheek retractor or intra-oral retractor 900 that is self-retainable for plastic surgeons and dentists is shown in FIG. 10. The cheek/oral retractor 900 is made of clear and flexible plastic and may be completely or partially illuminated. In FIG. 10, arrows indicated light from a reverse tear drop shaped FOLED 910 imbedded on the lingual side of retractor 900 with the buccal surface of the retractor acting to keep the retractor open and exposing the teeth. Of course, it should be appreciated that the FOLED may be utilized in other shapes depending on the type of retractor and procedure. Advantageously, the flexible and malleable nature of this type of retractor allows it to conform and/or be customized for a particular patient's anatomy and/or a particular surgeon's need.

OLED's are significant thinner and have a broader surface of illumination than other types of LED light systems typically used with surgical devices. In addition, OLED's produce a cool light compared to currently used fiber optics, which are hot, cumbersome and noisy. OLED's also have a longer battery life than currently used lighting systems. It should be appreciated that different types of OLED's may be incorporated to various types of retractors depending upon the particular application. Generally, a regular OLED is fabricated on a glass substrate. A flexible organic light emitting diode (FOLED) incorporates a flexible substrate instead of a glass substrate, such as metallic foils or thin plastics on which the electroluminescent organic semiconductor is deposited, which enables the device to be bent or rolled while still operating. Advantageously, the FOLED is bendable, lightweight and durable such that it may be used in a number of medical and surgical procedures. In more detail, the surface area (or part of the contact area) of the retractor is shapeable/malleable and illuminated by FOLED technology, which allows the retractor to be customizable to each patient's unique anatomy due to malleability. It should be appreciated that flexible electronics may be incorporated into the handle or blade of the retractor to complement the FOLEDs.

In another embodiment, a transparent organic light emitting diode (TOLED) may be used with the surgical device. Generally, an OLED has a bottom contact (or anode) having a transparent metal oxide film and a top contact (or cathode) made of a reflective metal. When light is generated by the OLED, it emits through the bottom transparent surface. In contrast, TOLEDs use an optically transparent top cathode, which allows both the top and bottom contacts to transmit light, which provides better illumination. Advantageously, a transparent portion of the retractor that is illuminated and flexible would allow the surgeon to not only customize (due to the malleable/flexible nature) and illuminate the surgical field but also provide the opportunity to have a transparent retractor (i.e., the surface area) to allow the surgeon to ensure that he/she does not damage, avulse or place undue pressure on the retracted tissues by direct observation.

In addition, a hybrid between the FOLED and TOLED may be used with the surgical device/retractor. Specifically, the flexible retraction surface has both the light (i.e., some type of OLED) and the clear, transparent and flexible housing or encasement. Thus, a flexible and illuminated retraction surface is created. Furthermore, a stack of TOLEDs known as a stacked organic light emitting diode (SOLED) may be used to improve resolution and enhance full-color quality. Finally, a phosphorescent organic light emitting diode (PHOLED) may be used with this technology because it has up to four times higher efficiency than a convention fluorescent OLED.

As shown in FIGS. 1 and 3, a surgical retractor 10, 200 generally has a handle portion 20, 220 at a first end and a blade portion 40, 240 at an opposite end. The blade portion is typically comprised of a thin walled, transparent, durable, light weight plastic. The components of the blade portion can be reprocessed using standard autoclave for sterility because the electronic components are completely encased. In addition, the plastic portion of the blade may be disposable and replaced, while a portion of the blade having the OLED or FOLED would be encased for sterilization purposes for reuse. The OLED or FOLED may be removed from the blade portion for replacement. In various embodiments, the blade may be part malleable plastic and malleable metal. For example, the teeth tips of a Weitlaner retractor may be malleable metal and the more bulky central teeth and retractor components may be malleable plastic. Thus, most of the tissue tension would fall on the metal portion instead of the plastic portion.

The handle 20, 220 is typically a hollow, light weight, metallic tube made of aluminum, steel, or other suitable material of that type that can be formed to the desired specification for the particular retractor. The handle houses the power supply 30 (i.e., battery or fuel cell) that will power the light emitter. The power supply 30 may be removable for replacement or recharging. It may also have at least one controller such as finger controls 100, 210 and 110, 230 for allowing the operator to control the OLED light emitter unit and a pair of polarized light panels in the housing, respectively. Both the intensity of the light and the opaqueness or translucence of the housing can be controlled by varying the voltage from the power supply to the OLED light emitter and to the polarized light panels via the finger controls. As a result, the intensity of the light in the surgical field can be altered by the operator/surgeon. In addition, the finger controls may vary the intensity of the light similar to a dimmer switch.

A light delivery system as used with the surgical retractor 10 typically includes: (1) an OLED light emitter unit 50; (2) a light encasement housing 60 connected to the distal end of the blade 40; and (3) a power supply 30, such as a battery or fuel cell. The light encasement housing 60 uses a conduction system from the power supply 30. The OLED light emitter unit 50 is typically positioned in the housing 60 of the blade portion 40 of the retractor 10 such that the retractor is a completely self-contained unit and does not require an external light source.

Figure 2:
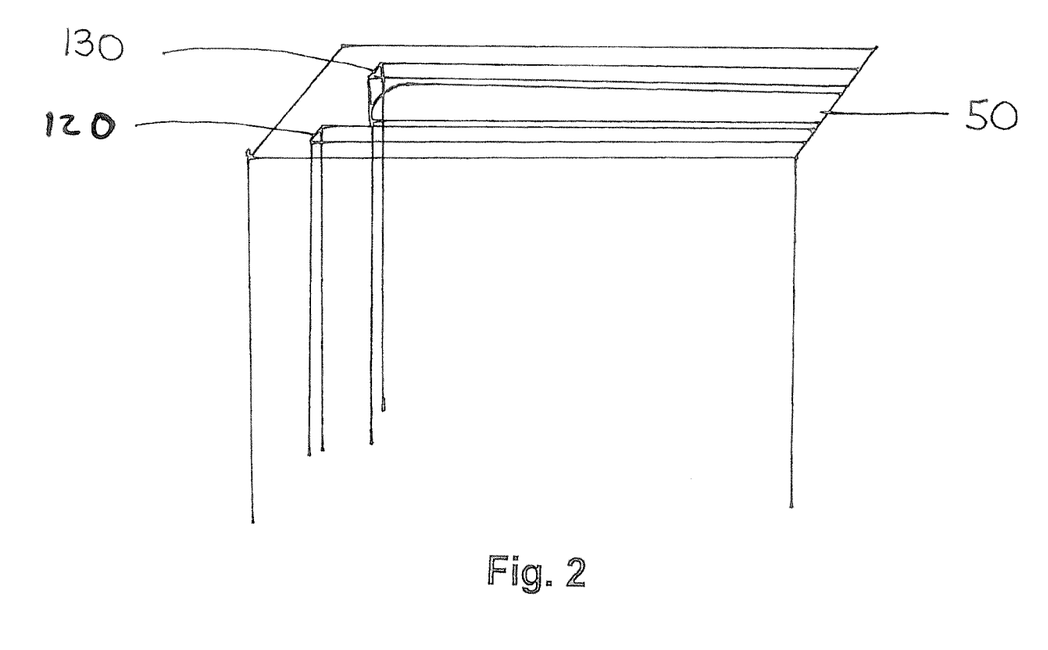
FIG. 2 is a cross-sectional view in accordance with one embodiment of the present invention of a retractor blade of the OLED illuminated retractor.

As shown in FIG. 2, a pair of substantially rectangular-shaped polarized OLED light emitter panels 120, 130 radiate light towards the surgical field in a uniformed intensity in a predetermined direction. As a result, an associated viewing field for the surgery/medical procedure is illuminated with a predetermined light characteristic. In addition, other types of direct light/zone lighting areas may be used with the surgical instrument to increase battery life. Flexible strips and groups of FOLEDs that can be selectively turned on and off would also increase battery life. An aperture, which is primarily used to gather light and resolve fine specimen detail at a fixed objective distance may be used in association with the pair of polarized light panels or in place of the panels. Advantageously, the aperture focuses the light to aid the physician performing the surgery/procedure. Of course, it should be appreciated that the aperture may only be suitable for use in certain type of retractors to selectively control the illuminated field and discriminate fine detail. The OLED light emitter unit 50 is typically positioned between the pair of polarized OLED light emitter panels 120, 130.

The OLED light emitter unit 50 may be substantially flat or suitably curved. Further, it may be formed of single or multiple layers and may have different thicknesses and shapes as appropriate for each type of surgical retractor. Moreover, the OLED light emitter unit 50 may be flexible or rigid, and may be made out of a variety of compounds. With these properties, it can be installed, encased or embedded in construction into the housing 60 in the various forms described above.

The light encasement housing 60 is comprised of a transparent or translucent light conducting plastic material of any suitable type, including acrylic, polycarbonate, glass, epoxy, resins or the like. It should also be appreciated that the OLED light emitter unit 50 will be protected in this section of the retractor 10 from contact with body fluids either, which reduces sterility concerns obvious in a surgical setting.

The pair of polarized light panels 120, 130 flank the OLED light emitter unit 50 in the housing 60 in order to help direct the light into the desired area of interest. The pair of polarized light panels may have a dichotomous function (i.e., on/off) to allow for direction of the OLED light emitter unit without directly altering the light intensity. Further, the OLED light emitter unit may have a separate control which may be based on a rheostat that will alter current to the OLED light emitter unit to directly change the intensity of the light in the field. The pair of polarized light panels may have separate controls and may share the power supply 30 with the light emitter unit 50. Advantageously, the pair of polarized light panels allow for variable direction of the light from the retractor blade. Further, multiple light configurations will be possible, such as illuminating both sides, single side illumination and no illumination.

The light encasement housing 60 has a first electric element 70 that conducts power from the power supply 30 in the handle 20 to the OLED light emitter 50. A second electric element 80 conducts power from the power supply 30 in the handle 20 to the pair of polarized light panels 120, 130. The light encasement housing 60 is typically made of the same transparent material that protects the OLED unit from body fluids. In the area of the encasement housing that is closest to the handle 20, there is a fastener system or locking coupler 90 that interlocks the encasement housing 60 to the handle 20. The fastener 90 will have two functions: (1) to provide a strong connection between the handle and retractor elements of the device; and (2) to electrically couple the power supply to the light emitter. In addition, a plurality of gaskets at the fastener may be used to ensure a water tight seal for the OLED and electrical elements of the device.

It should be appreciated that the surgical devices/retractors may be modified with various additional features depending on the particular application. For example, near infra-red technology may be incorporated into the retractor to identify vessels (i.e., blood flow and $O_2$ tension), especially tissue-specific retractors. In other embodiments, an integrated camera may be connected to a wireless hand-held device for review of the procedure. In addition, a suction device may be positioned on the side of a Richardson or Weitlaner retractor teeth. The suction device would be connected to a canister near the battery pack or attached to the wall suction. Finally, a LED may be positioned at the pivot point of the Weitlaner retractor to provide focused light and an OLED at the teeth/retractor portion to provide flood light illumination.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

The invention claimed is:

1. A retractor comprising:
a housing defining a blade portion and comprising:
a light system fully encased therein;
the light system comprising:
an organic light-emitting source to illuminate the blade portion;
a pair of longitudinally spaced-apart polarized light panels flanking the organic light-emitting source to pass polarized light from the light-emitting source to locations external to the blade portion, the spaced-apart polarized light panels to vary direction of the polarized light from the blade portion;
a separately-formed handle portion to accommodate a battery and one or more finger controls; and
a locking coupler, disposed between the housing and the separately-formed handle portion, to disengageably mechanically couple the handle portion to the housing and to electrically couple and decouple the one or more finger controls from the light system.

2. The retractor of claim 1, wherein the organic light source is an organic light emitting diode.

3. The retractor of claim 1, wherein the pair of polarized light panels are substantially rectangular-shaped.

4. The retractor of claim 1, wherein the separately-formed handle portion is configured to permit removal of the battery.

5. The retractor of claim 1, wherein the one or more finger controls are to vary intensity of light from the organic light-emitting source.

6. The retractor of claim 1, wherein the one or more finger controls are to vary opaqueness or translucence of polarized light panels.

7. The retractor of claim 1, wherein the organic light source and the pair of polarized light panels are configured to produce illumination of both sides of the blade portion or only a single side of the blade portion.

8. A retractor comprising:
a housing defining a blade portion and comprising:
a light system fully encased therein;
the light system comprising:
an organic light-emitting source to illuminate the blade portion;
a pair of longitudinally spaced-apart polarized light panels flanking the organic light-emitting source to pass polarized light from the light-emitting source to locations external to the blade portion, the spaced-apart polarized light panels to vary direction of the polarized light from the blade portion, wherein the organic light emitting diode unit extends along substantially an entire length of the pair of longitudinally spaced-apart polarized light panels such that light is emitted along an entire length of the organic light emitting diode unit;
a separately-formed handle portion to accommodate a battery and one or more finger controls; and
a locking coupler, disposed between the housing and the separately-formed handle portion, to disengageably mechanically couple the handle portion to the housing and to electrically couple and decouple the one or more finger controls from the light system.

9. The retractor of claim 8, wherein the one or more finger controls is to control the power supplied to the organic light emitting diode unit.

10. The retractor of claim 9, wherein the one or more finger controls is to control power supplied to the pair of polarized light panels.

11. The retractor of claim 8, wherein the blade portion is configured to be disposable.

12. The retractor of claim 8, wherein the housing includes a first electric element connecting the battery to the organic light-emitting source.

13. A retractor comprising:
a housing defining a blade portion and comprising:
  a light system fully encased therein;
  the light system comprising:
    an organic light-emitting source to illuminate the blade portion;
    a pair of longitudinally spaced-apart polarized light panels flanking the organic light-emitting source to pass polarized light from the light-emitting source to a surgical field external to the blade portion, the spaced-apart polarized light panels to vary direction of the polarized light from the blade portion;
a separately-formed handle portion to accommodate a battery and one or more finger controls disposed between the battery the one or more finger controls to control intensity and direction of the polarized light from the organic light-emitting source; and
a locking coupler, disposed between the housing and the separately-formed handle portion, to disengageably mechanically couple the handle portion to the housing and to electrically couple and decouple the one or more finger controls from the light system.

14. The retractor of claim 13, wherein the organic light source one or more organic light-emitting diodes.

15. The retractor of claim 13, wherein the pair of voltage-controlled polarized light panels are substantially rectangular-shaped.

16. The retractor of claim 13, wherein the separately-formed handle portion is configured to permit removal of the battery.

17. The retractor of claim 13, wherein the one or more finger controls comprises a dimming switch to vary the intensity of the organic light source.

18. The retractor of claim 13, wherein the spaced-apart polarized light panels are configured to produce multiple light configurations.

* * * * *